United States Patent
Berneth et al.

(10) Patent No.: US 6,641,889 B2
(45) Date of Patent: Nov. 4, 2003

(54) OPTICAL DATA STORAGE MEDIUM CONTAINING A TRIAZACYANINE DYE AS THE LIGHT-ABSORBING COMPOUND IN THE INFORMATION LAYER

(75) Inventors: Horst Berneth, Leverkusen (DE); Friedrich-Karl Bruder, Krefeld (DE); Wilfried Haese, Odenthal (DE); Rainer Hagen, Leverkusen (DE); Karin Hassenrück, Düsseldorf (DE); Serguei Kostromine, Swisttal (DE); Peter Landenberger, Köln (DE); Rafael Oser, Krefeld (DE); Thomas Sommermann, Bergisch Gladbach (DE); Josef-Walter Stawitz, Odenthal (DE); Thomas Bieringer, Odenthal (DE)

(73) Assignee: Bayer Aktiengesellschaft, Leverkusen (DE)

( * ) Notice: Subject to any disclaimer, the term of this patent is extended or adjusted under 35 U.S.C. 154(b) by 14 days.

(21) Appl. No.: 10/101,791

(22) Filed: Mar. 20, 2002

(65) Prior Publication Data
US 2002/0197439 A1 Dec. 26, 2002

(30) Foreign Application Priority Data

Mar. 28, 2001 (DE) .......................................... 101 15 227
Apr. 6, 2001 (DE) .......................................... 101 17 463

(51) Int. Cl.$^7$ ................................................. B32B 3/02
(52) U.S. Cl. ................. 428/64.1; 428/64.8; 430/270.15
(58) Field of Search ................. 428/64.1, 64.4, 428/64.8, 913; 430/270.15, 270.16, 495.1, 945

(56) References Cited

U.S. PATENT DOCUMENTS

| | | | |
|---|---|---|---|
| 3,166,606 A | 1/1965 | Reinking et al. | 260/860 |
| 5,043,403 A | 8/1991 | Dujardin et al. | 525/462 |
| 5,266,699 A | 11/1993 | Naef et al. | 546/61 |
| 5,356,857 A | 10/1994 | Vanmaele | 503/227 |
| 6,214,431 B1 | 4/2001 | Hua et al. | 428/64.1 |

FOREIGN PATENT DOCUMENTS

| | | |
|---|---|---|
| DE | 41 41 718 | 7/1993 |
| DE | 198 05 544 | 8/1999 |
| JP | 6-336086 | 12/1994 |
| JP | 8-191171 | 7/1996 |
| JP | 2 557335 | 11/1996 |
| JP | 9-50629 | 2/1997 |
| JP | 10-58828 | 3/1998 |
| JP | 10-181206 | 7/1998 |
| JP | 11-43481 | 2/1999 |

Primary Examiner—Elizabeth Mulvaney
(74) Attorney, Agent, or Firm—Godfried R. Akorli; Diderico van Eyll

(57) ABSTRACT

An optical data storage medium containing a preferably transparent substrate which has optionally already been coated with one or more reflecting layers and onto the surface of which a photorecordable information layer, optionally one or more reflecting layers, and optionally a protective layer or an additional substrate or a top layer are applied, which data storage medium can be recorded on and read using blue or red light, preferably laser light, wherein the information layer contains a light-absorbing compound and optionally a binder, characterized in that at least one triazacyanine dye is used as the light-absorbing compound.

8 Claims, 2 Drawing Sheets

Figure 1:
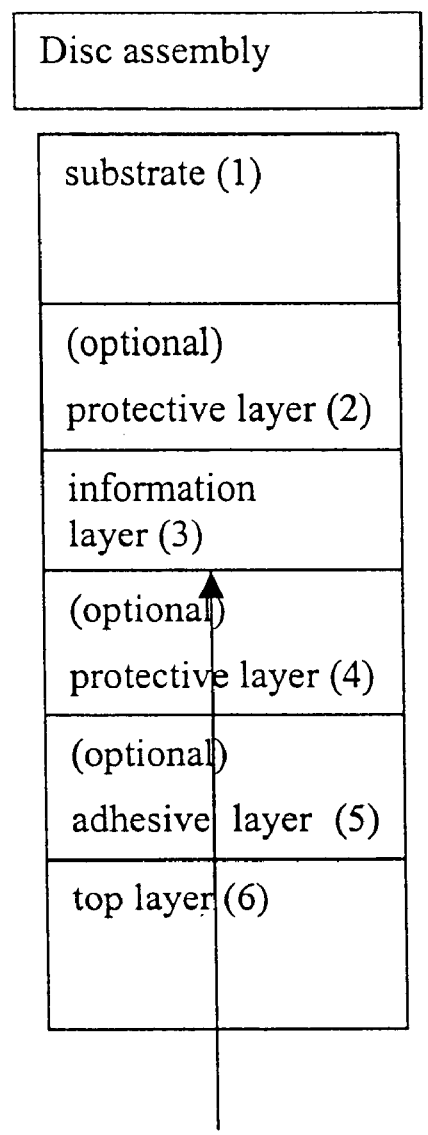

OPTICAL DATA STORAGE MEDIUM CONTAINING A TRIAZACYANINE DYE AS THE LIGHT-ABSORBING COMPOUND IN THE INFORMATION LAYER

The invention relates to a preferably once recordable optical data storage medium containing a triazacyanine dye as the light-absorbing compound in the information layer, and to a process for its production.

Recordable optical data storage media using special light-absorbing substances or mixtures thereof are particularly suitable for use in high-density recordable optical data storage media which operate with blue laser diodes, and in particular GaN or SHG laser diodes (360–460 nm), and/or for use in DVD-R or CD-R discs, which operate with red (635–660 nm) or infrared (780–830 nm) laser diodes, and the application of the abovementioned dyes to a polymer substrate, in particular polycarbonate, by spin-coating or vapour deposition.

There has recently been an enormous growth in the sales of recordable compact discs (CD-R, 780 nm), which represent the technically established system.

The next generation of optical data storage media—DVDs—is currently being introduced onto the market. By using shorter-wave laser radiation (635 to 660 nm) and a higher numerical aperture NA, the storage density can be increased. The recordable format is in this case the DVD-R.

Today, optical data storage formats which use blue laser diodes (based on GaN, JP 08191171 or Second Harmonic Generation SHG JP 09050629) (360 nm to 460 nm) with a high laser power, are being developed. Recordable optical data storage media will therefore also be used in this generation. The achievable storage density depends on the focussing of the laser spot in the information plane. The spot size is proportional to the laser wavelength $\lambda$/NA. NA is the numerical aperture of the objective lens used. The aim is to use the smallest possible wavelength $\lambda$ for obtaining the highest possible storage density. Based on semiconductor laser diodes, 390 nm are presently possible.

The patent literature describes dye-based recordable optical data storage media which are equally suitable both for CD-R and DVD-R systems (JP-A 11 043 481 and JP-A 10 181 206). In order to obtain high reflectivity, a high modulation level of the readout signal and sufficient sensitivity during recording, use is made of the fact that the IR wavelength 780 nm of the CD-R is located at the base of the long-wavelength slope of the absorption peak of the dye and the red wavelength 635 nm or 650 nm of the DVD-R is located at the base of the short-wavelength slope of the absorption peak of the dye. In JP-A 02 557 335, JP-A 10 058 828, JP-A 06 336 086, JP-A 02 865 955, WO-A 09 917 284 and U.S. Pat. No. 5,266,699 this concept is extended to cover the working wavelength range of 450 nm on the short-wavelength slope and the red and IR range on the long-wavelength slope of the absorption peak.

In addition to the abovementioned optical properties, the recordable information layer consisting of light-absorbing organic substances must have a morphology which is as amorphous as possible, in order to keep the noise signal during recording or reading as small as possible. For this purpose it is particularly preferable, when applying the substances by spin-coating from a solution or by vapour deposition and/or sublimation, to prevent crystallization of the light-absorbing substances during the subsequent top-coating with metallic or dielectric layers in vacuo.

The amorphous layer of light-absorbing substances should preferably have high thermal stability, since otherwise additional layers of organic or inorganic material applied by sputtering or vapour deposition onto the light-absorbing information layer form blurred boundaries due to diffusion and thus have an adverse effect on the reflectivity. In addition, if a light-absorbing substance has inadequate thermal stability at the boundary to a polymeric substrate, it can diffuse into the latter and again have an adverse effect on the reflectivity.

If the light-absorbing substance has too high a vapour pressure, it can sublime during the abovementioned sputtering or vapour deposition of additional layers in a high vacuum and thus reduce the desired layer thickness. This in turn has a negative effect on reflectivity.

The object of the invention is therefore to provide suitable compounds which meet the high demands (such as light stability, a favourable signal-to-noise ratio, damage-free application to the substrate material, etc.) for use in the information layer of a recordable optical data storage medium, in particular for high-density recordable optical data storage formats in a laser wavelength range of 340 to 680 nm.

Surprisingly, it has been found that light-absorbing compounds from the triazacyanine group of dyes are particularly suitable for satisfying the abovementioned requirement profile.

The invention therefore relates to an optical data storage medium containing a preferably transparent substrate which has optionally already been coated with one or more reflecting layers and onto the surface of which a photorecordable information layer, optionally one or more reflecting layers and optionally a protective layer or an additional substrate or a top layer are applied, which data storage medium can be recorded on and read using blue or red light, preferably laser light, wherein the information layer contains a light-absorbing compound and optionally a binder, characterized in that at least one triazacyanine dye is used as the light-absorbing compound.

The light-absorbing compound should preferably be thermally modifiable. Preferably the thermal modification is carried out at a temperature of <600° C., particularly preferably at a temperature of <400° C., very particularly preferably at a temperature of <300° C., and in particular at a temperature of <200° C. Such a modification can for example be the decomposition or chemical modification of the chromophoric centre of the light-absorbing compound.

A triazacyanine of the formula I is preferred

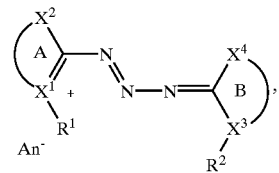

(I)

in which $X^1$ and $X^3$ represent nitrogen or $X^1$—$R^1$ and $X^3$—$R^2$ independently of one another represent S, $X^2$ and $X^4$ independently of one another represent O, S, CH or N—$R^3$, $R^1$, $R^2$ and $R^3$ independently of one another represent $C_1$- to $C_{16}$-alkyl, $C_3$- to $C_6$-alkenyl, $C_5$- to $C_7$-cycloalkyl or $C_7$- to $C_{16}$-aralkyl, the rings A and B, each together with $X^1$, $X^2$ and $X^3$, $X^4$, respectively, and the C atom in each case bound therebetween, independently of one another represent a five- or six-membered aromatic or quasiaromatic heterocyclic ring, which can contain 1 to 4 hetero atoms and/or can be benzo- or naphtho-fused and/or substituted by non-ionic radicals, and An⁻ represents an anion.

Suitable non-ionic radicals are for example $C_1$- to $C_4$-alkyl, $C_1$- to $C_4$-alkoxy, halogen, cyano, nitro, $C_1$- to $C_4$-alkoxycarbonyl, $C_1$- to $C_4$-alkylthio, $C_1$- to $C_4$-alkanoylamino, benzoylamino and mono- or di-$C_1$- to $C_4$-alkylamino.

Alkyl, alkoxy, aryl and heterocyclic radicals can optionally contain additional radicals such as alkyl, halogen, nitro, cyano, CO—NH₂, alkoxy, trialkylsilyl, trialkylsiloxy or phenyl, the alkyl and alkoxy radicals can be straight-chain or branched, the alkyl radicals can be partially halogenated or perhalogenated, the alkyl and alkoxy radicals can be ethoxylated or propoxylated or silylated, adjacent alkyl and/or alkoxy radicals on aryl or heterocyclic radicals can together form a three- or four-membered bridge and the heterocyclic radicals can be benzo-fused and/or quaternized.

Particulary preferably the ring A of the formula

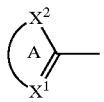

(II)

represents benzothiazol-2-yl, benzoxazol-2-yl, benzimidazol-2-yl, thiazol-2-yl, isothiazol-3-yl, imidazol-2-yl, pyrazol-5-yl, 1,3,4-thiadiazol-2-yl, 1,2,4-thiadiazol-5-yl, 1,2,3-thiadiazol-5-yl, 1,3,4-triazol-2-yl, 2- or 4-pyridyl or 2- or 4-quinolyl, wherein the aforementioned rings can optionally be substituted by $C_1$- to $C_6$-alkyl, $C_1$- to $C_6$-alkoxy, fluorine, chlorine, bromine, iodine, cyano, nitro, $C_1$- to $C_6$-alkoxy-carbonyl, $C_1$- to $C_6$-alkylthio, $C_1$- to $C_6$-acylamino, $C_6$- to $C_{10}$-aryl, $C_6$- to $C_{10}$-aryloxy, $C_6$- to $C_{10}$-arylcarbonylamino, mono- or di-$C_1$- to $C_6$-alkylamino, N—$C_1$- to $C_6$-alkyl-N—$C_6$- to $C_{10}$-arylamino, pyrrolidino, morpholino or piperazino, and the ring B of the formula

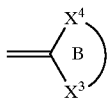

(III)

represents benzothiazol-2-ylidene, benzoxazol-2-ylidene, benzimidazol-2-ylidene, thiazol-2-ylidene, isothiazol-3-ylidene, imidazol-2-ylidene, pyrazol-5-ylidene, 1,3,4-thiadiazol-2-ylidene, 1,2,4-thiadiazol-5-ylidene, 1,2,3-thiadiazol-5-ylidene, 1,3,4-triazol-2-ylidene, pyridin-2- or 4-ylidene, quinolin-2- or 4-ylidene, wherein the aforementioned rings can in each case be substituted by $C_1$- to $C_6$-alkyl, $C_1$- to $C_6$-alkoxy, fluorine, chlorine, bromine, iodine, cyano, nitro, $C_1$- to $C_6$-alkoxycarbonyl, 5 $C_1$- to $C_6$-alkylthio, $C_1$- to $C_6$-acylamino, $C_6$- to $C_{10}$-aryl, $C_6$- to $C_{10}$-aryloxy, $C_6$- to $C_{10}$-arylcarbonylamino, mono- or di-$C_1$- to $C_6$-alkylamino, N—$C_1$- to $C_6$-alkyl-N—$C_6$- to $C_{10}$-arylamino, pyrrolidino, morpholino or piperazino.

In a particularly preferred form the triazacyanines are those of the formula

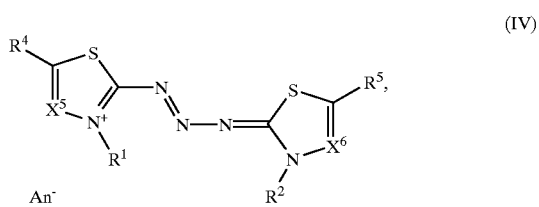

(IV)

wherein $R^1$ and $R^2$ independently of one another represent $C_1$- to $C_{16}$-alkyl, $C_3$- to $C_6$-alkenyl, $C_5$- to $C_7$-cycloalkyl or $C_7$- to $C_{16}$-aralkyl, $X^5$ represents N or C—$R^6$, $X^6$ represents N or C—$R^7$, $R^4$ to $R^7$ independently of one another represent hydrogen, $C_1$- to $C_4$-alkyl, $C_1$- to $C_4$-alkoxy, $C_1$- to $C_4$-alkylthio, cyano, $C_1$- to $C_4$-alkoxycarbonyl, nitro, mono- or bis-$C_1$- to $C_4$-alkylamino, N—$C_1$- to $C_4$-alkyl-N—$C_7$- to $C_{15}$-aralkylamino, N—$C_1$- to $C_4$-alkyl-N—$C_5$- to $C_{17}$-cycloalkylamino, N—$C_1$- to $C_4$-alkyl-N—$C_6$- to $C_{10}$-arylamino, $C_6$- to $C_{10}$-arylamino, pyrrolidino, piperidino, piperazino or morpholino or $R^4;R^6$ and $R^5;R^7$ independently of one another form a —CH=CH—CH=CH— bridge which can be substituted by methyl, chlorine, methoxy or cyano and $An^{31}$ represents an anion.

Suitable anions An⁻ are all monovalent anions or one equivalent of a polyvalent anion. Preferably the anions are colourless. Suitable anions are for example chloride, bromide, iodide, tetrafluoroborate, perchlorate, hexafluorosilicate, hexafluorophosphate, methosulphate, ethosulphat, $C_1$- to $C_{10}$-alkanesulphonate, $C_1$- to $C_{10}$-perfluoroalkane sulphonate, $C_1$- to $C_{10}$-alkanoate optionally substituted by chlorine, hydroxyl or $C_1$- to $C_4$ alkoxy, benzene sulphonate, naphthalene sulphonate or biphenyl sulphonate optionally substituted by nitro, cyano, hydroxyl, $C_1$- to $C_{25}$-alkyl, perfluoro-$C_1$- to $C_4$-alkyl, $C_1$- to $C_4$-alkoxycarbonyl or chlorine, benzene disulphonate, naphthalene disulphonate or biphenyl disulphonate optionally substituted by nitro, cyano, hydroxyl, $C_1$- to $C_4$-alkyl, $C_1$- to $C_4$-alkoxy, $C_1$- to $C_4$-alkoxycarbonyl or chlorine, benzoate optionally substituted by nitro, cyano, $C_1$- to $C_4$-alkyl, $C_1$- to $C_4$-alkoxy, $C_1$- to $C_4$-alkoxycarbonyl, benzoyl, chlorobenzoyl or toluoyl, the anion of naphthalenedicarboxylic acid, diphenyl ether disulphonate, tetraphenyl borate, cyanotriphenyl borate, tetra-$C_1$- to $C_{20}$-alkoxyborate, tetraphenoxyborate, 7,8- or 7,9-dicarba-nido-undecaborate (1-) or (2-), which are optionally substituted on the B- and/or C-atoms by one or two $C_1$- to $C_{12}$-alkyl or phenyl groups, dodecahydro-dicarbadodecaborate(2-) or B—$C_1$- to $C_{12}$-alkyl-C-phenyl-dodecahydro-dicarbadodecaborate(1-).

Bromide, iodide, tetrafluoroborate, perchlorate, methane sulphonate, benzene sulphonate, toluene sulphonate, dodecylbenzene sulphonate and tetradecane sulphonate are preferred.

In a very particularly preferred form the triazacyanines used are those of the formula (IV), wherein $R^1$ and $R^2$ independently of one another represent methyl, ethyl, propyl, butyl, pentyl, hexyl, benzyl, cyclohexyl, chloroethyl, cyanomethyl, cyanoethyl, hydroxyethyl, 2-hydroxypropyl, methoxyethyl, ethoxyethyl or a radical of the formula

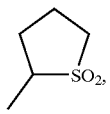

$X^5$ represents N or C—$R^6$,
$X^6$ represents N or C—$R^7$,
$R^4$ and $R^5$ independently of one another represent hydrogen, methyl, ethyl, methoxy, cyano, methoxycarbonyl, dimethylamino, diethylamino, dipropylamino, dibutylamino, N-methyl-N-cyanoethylamino, N-methyl-N-methoxyethylamino, N-methyl-N-hydroxyethylamino, bis-(cyanoethyl)amino, bis-(methoxyethyl)amino, bis-(hydroxyethyl)-amino, N-methyl-N-benzylamino, N-methyl-N-phenylamino, phenyl-amino, methoxyphenylamino, pyrrolidino, piperidino, N-methyl-, N-ethyl-, N-hydroxyethyl- or N-cyanoethylpiperazino or morpholino,
$R^6$ and $R^7$ independently of one another represent hydrogen, methyl, ethyl, methoxy or cyano or
$R^4$;$R^6$ and $R^5$;$R^7$ independently of another form a —CH=CH—CH=CH— bridge, which can be substituted by methyl, chlorine, methoxy or cyano, and
An⁻ represents an anion.

In a form which is also eminently preferred the triazacyanines used are those of the formula (IV),
wherein
$R^1$ and $R^2$ are identical and represent methyl, ethyl, propyl, butyl, pentyl, hexyl, benzyl, cyclohexyl, chloroethyl, cyanomethyl, cyanoethyl, hydroxy-ethyl, 2-hydroxypropyl, methoxyethyl, ethoxyethyl or a radical of the formula

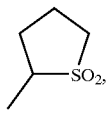

$X^5$ represents C—$R^6$,
$X^6$ represents C—$R^7$,
$R^4$;$R^6$ and $R^5$;$R^7$ are identical and form a —CH=CH—CH=CH— bridge, which can be substituted by methyl, chlorine, methoxy or cyano, and
An⁻ represents an anion.

In a form which is also eminently preferred the triazacyanines used are those of the formula (IV),
wherein
$R^1$ and $R^2$ are identical and represent methyl, ethyl, propyl, butyl, pentyl, hexyl, benzyl, cyclohexyl, chloroethyl, cyanomethyl, cyanoethyl, hydroxy-ethyl, 2-hydroxypropyl, methoxyethyl, ethoxyethyl or a radical of the formula

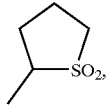

$X^5$ represents N,
$X^6$ represents N,
$R^4$ and $R^5$ are identical and represent dimethylamino, diethylamino, dipropylamino, dibutylamino, N-methyl-N-cyanoethylamino, N-methyl-N-methoxyethylamino, N-methyl-N-hydroxyethylamino, bis-(cyanoethyl)amino, bis-(methoxyethyl)amino, bis-(hydroxyethyl)-amino, N-methyl-N-benzylamino, N-methyl-N-phenylamino, phenyl-amino, methoxyphenylamino, pyrrolidino, piperidino, N-methyl-, N-ethyl-, N-hydroxyethyl- or N-cyanoethylpiperazino or morpholino, and
An⁻ represents an anion.

In a form which is also eminently preferred the triazacyanines used are those of the formula (IV),
wherein
$R^1$ and $R^2$ are identical and represent methyl, ethyl, propyl, butyl, pentyl, hexyl, benzyl, cyclohexyl, chloroethyl, cyanomethyl, cyanoethyl, hydroxy-ethyl, 2-hydroxypropyl, methoxyethyl, ethoxyethyl or a radical of the formula

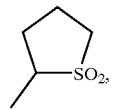

$X^5$ represents N,
$X^6$ represents C—$R^7$,
$R^4$ represents dimethylamino, diethylamino, dipropylamino, dibutylamino, N-methyl-N-cyanoethylamino, N-methyl-N-methoxy-ethylamino, N-methyl-N-hydroxyethylamino, bis-(cyanoethyl)amino, bis-(methoxyethyl)amino, bis-(hydroxyethyl)amino, N-methyl-N-benzylamino, N-methyl-N-phenylamino, phenylamino, methoxy-phenylamino, pyrrolidino, piperidino, N-methyl-, N-ethyl-, N-hydroxyethyl- or N-cyanoethylpiperazino or morpholino,
$R^5$;$R^7$ forms a —CH=CH—CH=CH—bridge, which can be substituted by methyl, chlorine, methoxy or cyano, and
An⁻ represents an anion.

For a recordable optical data storage medium according to the invention which is recorded on and read using light from a blue laser, such triazacyanine dyes are preferred whose absorption maximum $\lambda_{max2}$ is in the range from 420 to 550 nm, wherein the wavelength $\lambda_{1/2}$ at which the extinction on the short-wavelength slope of the absorption maximum of the wavelength $\lambda_{max2}$ is half the extinction value at $\lambda_{max2}$, and the wavelength $\lambda_{1/10}$, at which the extinction on the short-wavelength slope of the absorption maximum of the wavelength $\lambda_{max2}$ is a tenth of the extinction value at $\lambda_{max2}$, are preferably in each case no further than 50 nm away from each other. Preferably such a triazacyanine dye does not display a shorter-wave maximum $\lambda_{max1}$ at a wavelength below 350 nm, particularly preferably below 320 nm, and very particularly preferably below 290 nm.

Preferred triazacyanine dyes are those with an absorption maximum $\lambda_{max2}$ of 410 to 530 nm.

Particularly preferred triazacyanine dyes are those with an absorption maximum $\lambda_{max2}$ of 420 to 510 nm.

Very particularly preferred triazacyanine dyes are those with an absorption maximum $\lambda_{max2}$ of 430 to 500 nm.

In these triazacyanine dyes $\lambda\frac{1}{2}$ and $\lambda\frac{1}{10}$, as defined above, are preferably no further than 40 nm, particularly preferably no further than 30 nm, and very particularly preferably no further than 20 nm away from each other.

For a recordable optical data storage medium according to the invention which is recorded on and read using light from a red laser, such triazacyanine dyes are preferred whose absorption maximum $\lambda_{max2}$ is in the range from 500 to 650 nm, wherein the wavelength $\lambda_{1/2}$ at which the extinction on the long-wavelength slope of the absorption maximum of the wavelength $\lambda_{max2}$ is half the extinction value at $\lambda_{max2}$ and the wavelength $\lambda_{1/10}$, at which the extinction on the long-wavelength slope of the absorption maximum of the wavelength $\lambda_{max2}$ is a tenth of the extinction value at $\lambda_{max2}$, are preferably in each case no further than 50 nm away from each other. Preferably such a triazacyanine dye does not display a longer-wave maximum $\lambda_{max3}$ at a wavelength below 750 nm, particularly preferably below 800 nm, and very particularly preferably below 850 nm.

Preferred triazacyanine dyes are those with an absorption maximum $\lambda_{max2}$ of 530 to 630 nm.

Particularly preferred triazacyanine dyes are those with an absorption maximum $\lambda_{max2}$ of 550 to 620 nm.

Very particularly preferred triazacyanine dyes are those with an absorption maximum $\lambda_{max2}$ of 580 to 610 nm.

In these triazacyanine dyes $\lambda\frac{1}{2}$ and $\lambda\frac{1}{2}$, as defined above, are preferably no further than 40 nm, particularly preferably no further than 30 nm, and very particularly preferably no further than 20 nm away from each other.

At the absorption maximum $\lambda_{max2}$ the triazacyanine dyes have a molar extinction coefficient $\epsilon$ of >20000 l/mol cm, preferably >30000 l/mol cm, particularly preferably >40000 l/mol cm and very particularly preferably >60000 l/mol cm.

The absorption spectra are, for example, measured in solution.

Triazacyanines of the formula (I) are known, for example, from EP-A 0 567 846.

The light-absorbing substances described guarantee sufficiently high reflectivity (>10%) of the optical data storage medium in the unrecorded state and sufficiently high absorption for the thermal degradation of the information layer upon spotwise illumination with focussed light, if the wavelength of the light is in the range from 360 to 460 nm and 600 to 680 nm. The contrast between the recorded and unrecorded areas of the data storage medium is effected by the change in reflectivity in terms of the amplitude as well as the phase of the incident light as a result of the changed optical properties of the information layer following thermal degradation.

The triazacyanine dyes according to the invention especially guarantee a particularly high change in the refractive index upon the transition from the unrecorded to the recorded state.

The triazacyanine dyes are preferably applied to the optical data storage medium by spin-coating. The triazacyanines can be mixed with other triazacyanines or with other dyes having similar spectral properties. The information layer can contain additives in addition to the triazacyanine dyes, such as binders, wetting agents, stabilizers, diluents and sensitizers as well as other constituents.

In addition to the information layer, the optical data storage medium can contain other layers such as metal layers, dielectric layers and protective layers. Metals and dielectric layers are used, for example, for adjusting the reflectivity and the thermal balance. Depending on the laser wavelength, the metals can be gold, silver or aluminium, etc. Dielectric layers are, for example, silicon dioxide and silicon nitride. Protective layers are, for example, photocurable surface coatings, (pressure-sensitive) adhesive layers and protective films.

Preferred pressure-sensitive adhesive layers mainly consist of acrylic adhesives. Nitto Denko DA-8320 or DA-8310 which are disclosed in the patent JP-A 11-273147, can for example be used for this purpose.

The optical data storage medium has, for example, the following layer assembly (cf. FIG. 1): a transparent substrate (1), optionally a protective layer (2), an information layer (3), optionally a protective layer (4), optionally an adhesive layer (5) and a top layer (6).

Preferably, the optical data storage medium assembly can contain:

a preferably transparent substrate (1), onto whose surface at least one photorecordable information layer (3), which can be recorded on using light, preferably laser light, optionally a protective layer (4), optionally an adhesive layer (5) and a transparent top layer (6) are applied;

a preferably transparent substrate (1), onto whose surface a protective layer (2), at least one information layer (3) which can be recorded on using light, preferably laser light, optionally an adhesive layer (5) and a transparent top layer (6) are applied;

a preferably transparent substrate (1), onto whose surface optionally a protective layer (2), at least one information layer (3) which can be recorded on using light, preferably laser light, optionally a protective layer (4), optionally an adhesive layer (5) and a transparent top layer (6) are applied;

a preferably transparent substrate (1), onto whose surface at least one information layer (3) which can be recorded on using light, preferably laser light, optionally an adhesive layer (5) and a transparent top layer (6) are applied.

Figure 2:
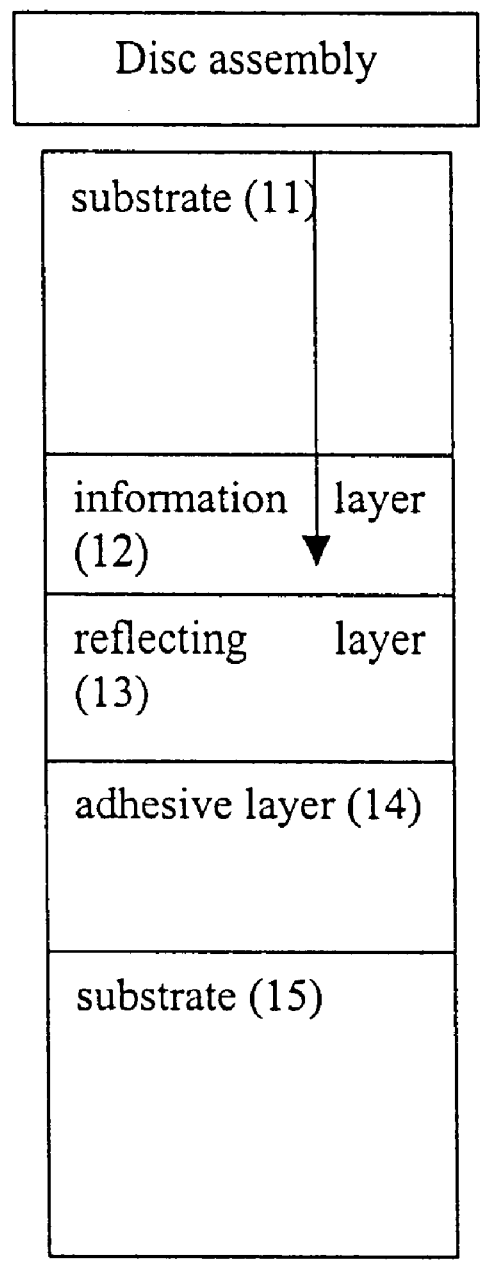

Alternatively the optical data storage medium has for example the following layer assembly (cf. FIG. 2): a preferably transparent substrate (11), an information layer (12), optionally a reflecting layer (13), optionally an adhesive layer (14) and an additional, preferably transparent, substrate (15).

The invention also relates to optical data storage media according to the invention which are recorded on using blue or red light, and in particular laser light.

The following examples illustrate the subject matter of the invention:

EXAMPLES

Example 1 a) 41.6 g of dimethyl sulphate were added at 80° C. to 45 g of 2-aminobenzothiazole in 500 ml of toluene over a period of 30 mins. After 1 h at 80° C. the suspension was cooled, filtered off with suction and the residue was washed with toluene. The solid was dissolved in 300 ml of water. By adding a concentrated KOH solution the pH was raised to 9. After stirring for 6 h at room temperature the precipitated product was filtered off by suction, washed with water and dried. 42.9 g (87% of theory) of a colourless crystallizate of the formula

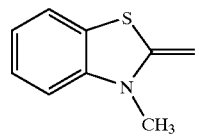

were obtained.

b) 30 g of 2-aminobenzothiazole were dissolved in 400 ml of glacial acetic acid and 80 ml of 85 wt. % phosphoric acid and 60 ml of 48 wt. % sulphuric acid were added at 10° C. 68 g of nitrosylsulphuric acid (40 wt. % in sulphuric acid) were added dropwise at 5° C. After 4 h at 0–5° C. the nitrite excess was destroyed with amidosulphonic acid.

c) The diazotized product from b) was added dropwise to a solution of 32.8 g of the product from a) in 240 ml of glacial acetic acid at 3° C., the pH being kept at 3 by the dropwise addition of a 20 wt. % soda solution. Finally, the mixture was adjusted to a pH of 3.5 and stirred overnight at room temperature. The product was filtered off by suction and washed with water. It was beaten into 300 ml of water, adjusted to a pH of 7.5 with a 20 wt. % soda solution, filtered off by suction once again, washed with water and dried. 29.7 g (46% of theory) of a yellow powder of the formula

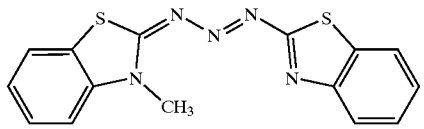

were obtained.

d) 4 ml of dimethyl sulphate were added at 80° C. to 8.8 g of the triazene from c) in 40 ml of γ-butyrolactone. After 6 h at 80° C. the mixture was cooled, discharged onto 500 ml of water and the insoluble constituents were removed by filtration.

e) 6.6 g of sodium tetrafluoroborate were added to the solution from d) at room temperature. After stirring overnight, the mixture was filtered off by suction and the residue was washed with water. The orange solid was stirred successively in 50 ml of methanol, 50 ml of ethyl acetate and 10 ml of water, filtered off by suction each time and dried. 2.4 g (28% of theory) of an orange powder of the formula

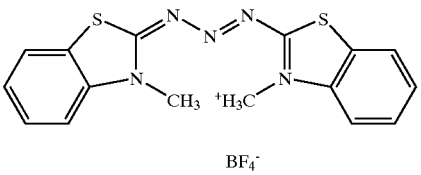

were obtained.

M.p.=260–266° C.

$\lambda_{max}$ (methanol/chloroform 1:1)=489 nm $\epsilon$=33280 l/mol cm $\lambda_{1/2}-\lambda_{1/10}$(short-wavelength slope)=61 nm $\lambda_{1/2}-\lambda_{1/10}$(long-wavelength slope)=16 nm Solubility: >2% in TFP (2,2,3,3-tetrafluoropropanol)

a glassy film.

Triazacyanine dyes which are also suitable are listed in the table.

| Example | R$^1$ | R$^2$ | An$^-$ | $\lambda_{max}$/nm[1] | $\epsilon$/l/mol cm | $\lambda_{1/2}-\lambda_{1/10}$/nm |
|---|---|---|---|---|---|---|
| 2 | | | BF$_4^-$ | 500 | 33290 | 62.5[2]<br>22[3] |
| 3 | | | I$^-$ | 50 | 33290 | |
| 4 | | | BF$_4^-$ | 492 | 33250 | |
| 5 | | | ClO$_4^-$ | 452 | | |

-continued
| Example | A ring (R¹) | B ring (R²) | An⁻ | $\lambda_{max}$/nm[1] | $\epsilon$/l/mol cm | $\lambda_{1/2}-\lambda_{1/10}$/nm |
|---|---|---|---|---|---|---|
| 6 | 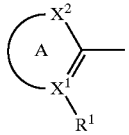 | 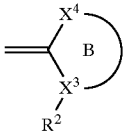 | BF$_4^-$ | 430 | | |
| 7 | 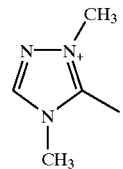 | 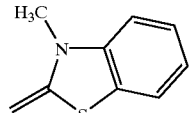 | BF$_4^-$ | 496 | | |
| 8 | 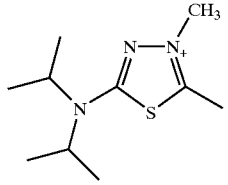 | 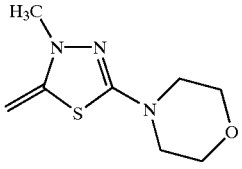 | BF$_4^-$ | 465 | | |
| 9 | 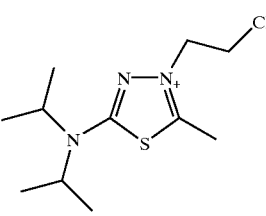 | 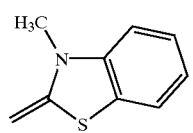 | PF$_6^-$ | 490 | | |
| 10 | 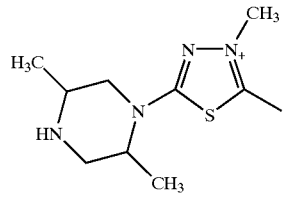 | 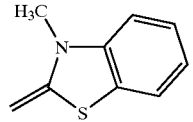 | BF$_4^-$ | 505 | | |
| 11 | 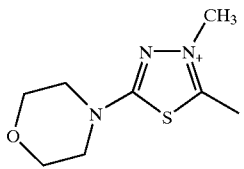 | 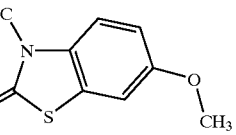 | BF$_4^-$ | 490 | | |
| 12 | 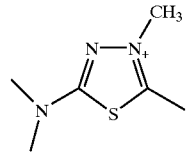 | 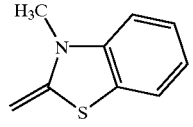 | BF$_4^-$ | 492 | | |

-continued

| Example | A (R¹) | B (R²) | An⁻ | $\lambda_{max}$/nm[1] | $\epsilon$/l/mol cm | $\lambda_{1/2}-\lambda_{1/10}$/nm |
|---|---|---|---|---|---|---|
| 13 | 2-dimethylamino-4-benzyl-5-methyl-1,3,4-thiadiazolium | 3-methyl-2-methylene-benzothiazoline | PF₆⁻ | 498 | | |
| 14 | 2-phenylamino-3-methyl-5-methyl-1,3,4-thiadiazolium | 3-methyl-2-methylene-benzothiazoline | BF₄⁻ | 498 | | |
| 15 | 2-(N-methyl-N-phenylamino)-3-methyl-5-methyl-1,3,4-thiadiazolium | 3-methyl-2-methylene-benzothiazoline | BF₄⁻ | 500 | | |
| 16 | 2-morpholino-3-methyl-5-methyl-1,3,4-thiadiazolium | 2-morpholino-3-methyl-5-methylene-1,3,4-thiadiazoline | BF₄⁻ | 494 | | |
| 17 | 2-(N-methyl-N-hydroxyethylamino)-3-methyl-5-methyl-1,3,4-thiadiazolium | 3-methyl-2-methylene-benzothiazoline | BF₄⁻ | 496 | | |
| 18 | 2-(N-methyl-N-cyanoethylamino)-3-methyl-5-methyl-1,3,4-thiadiazolium | 3-methyl-2-methylene-benzothiazoline | BF₄⁻ | 490 | | |
| 19 | 2-(N,N-bis(cyanoethyl)amino)-3-methyl-5-methyl-1,3,4-thiadiazolium | 3-methyl-2-methylene-benzothiazoline | Br⁻ | 488 | | |

-continued

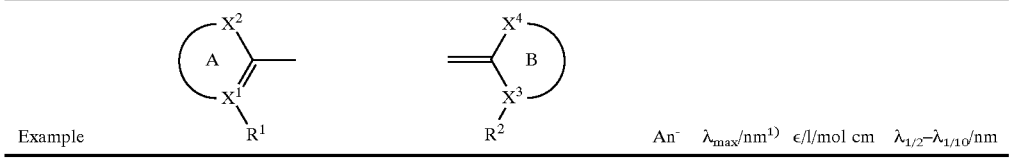

| Example | | | An$^-$ | $\lambda_{max}$/nm[1] | $\epsilon$/l/mol cm | $\lambda_{1/2}$–$\lambda_{1/10}$/nm |

[1] in methanol, unless otherwise specified.
[2] on the short-wavelength slope
[3] on the long-wavelength slope

What is claimed is:

1. An optical data storage medium containing a preferably transparent substrate which has optionally already been coated with one or more reflecting layers and onto whose surface a photorecordable information layer, optionally one or more reflecting layers and optionally a protective layer or an additional substrate or a top layer are applied, which data storage medium can be recorded on and read using blue or red light, preferably laser light, wherein the information layer contains a light-absorbing compound and optionally a binder, characterized in that at least one triazacyanine dye is used as the light-absorbing compound.

2. An optical data storage medium according to claim 1, characterized in that the triazacyanine corresponds to the formula

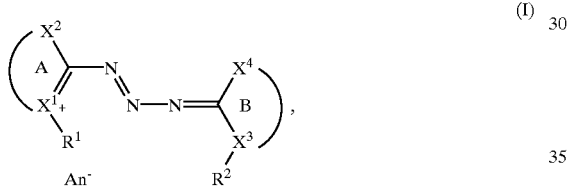

(I)

wherein $X^1$ and $X^3$ represent nitrogen or $X^1$—$R^1$ and $X^3$—$R^2$ independently of one another represent S, $X^2$ and $X^4$ independently of one another represent O, S, CH or N—$R^3$, $R^1$, $R^2$ and $R^3$ independently of one another represent $C_1$- to $C_{16}$-alkyl, $C_3$- to $C_6$-alkenyl, $C_5$- to $C_7$-cycloalkyl or $C_7$- to $C_{16}$-aralkyl, the rings A and B, in each case together with $X^1$, $X^2$ and $X^3$, $X^4$, respectively, and the C atoms in each case bound therebetween, independently of one another represent a five- or six-membered aromatic or quasiaromatic heterocyclic ring which can contain 1 to 4 hetero atoms and/or can be benzo- or naphtho-fused and/or substituted by non-ionic radicals and An$^-$ represents an anion.

3. An optical data storage medium according to claim 2, characterized in that the ring A of the formula

(II)

represents benzothiazol-2-yl, benzoxazol-2-yl, benzimidazol-2-yl, thiazol-2-yl, isothiazol-3-yl, imidazol-2-yl, pyrazol-5-yl, 1,3,4-thiadiazol-2-yl, 1,2,4-thiadiazol-5-yl, 1,2,3-thiadiazol-5-yl, 1,3,4-triazol-2-yl, 2- or 4-pyridyl, or 2-or 4-quinolyl, it being possible for the aforementioned rings to be in each case substituted by $C_1$- to $C_6$-alkyl, $C_1$- to $C_6$-alkoxy, fluorine, chlorine, bromine, iodine, cyano, nitro, $C_1$- to $C_6$-alkoxycarbonyl, $C_1$- to $C_6$-alkylthio, $C_1$- to $C_6$-acylamino, $C_6$- to $C_{10}$-aryl, $C_6$- to $C_{10}$-aryloxy, $C_6$- to $C_{10}$-arylcarbonylamino, mono- or di-$C_1$- to $C_6$-alkylamino, N—$C_1$- to $C_6$-alkyl-N—$C_6$- to $C_{10}$-arylamino, pyrrolidino, morpholino or piperazino, and the ring B of the formula

(III)

represents benzothiazol-2-ylidene, benzoxazol-2-ylidene, benzimidazol-2-ylidene, thiazol-2-ylidene, isothiazol-3-ylidene, imidazol-2-ylidene, pyrazol-5-ylidene, 1,3,4-thiadiazol-2-ylidene, 1,2,4-thiadiazol-5-ylidene, 1,2,3-thiadiazol-5-ylidene, 1,3,4-triazol-2-ylidene, pyridin-2- or 4-ylidene or quinolin-2- or 4-ylidene, it being possible for the aforementioned rings to be in each case substituted by $C_1$- to $C_6$-alkyl, $C_1$- to $C_6$-alkoxy, fluorine, chlorine, bromine, iodine, cyano, nitro, $C_1$- to $C_6$-alkoxycarbonyl, $C_1$- to $C_6$-alkylthio, $C_1$- to $C_6$-acylamino, $C_6$- to $C_{10}$-aryl, $C_6$- to $C_{10}$-aryloxy, $C_6$- to $C_{10}$-arylcarbonylamino, mono- or di-$C_1$- to $C_6$-alkylamino, N—$C_1$- to $C_6$-alkyl-N—$C_6$- to $C_{10}$-arylamino, pyrrolidino, morpholino or piperazino.

4. An optical data storage medium according to one or more of claims 1 to 3, characterized in that the triazacyanine corresponds to the formula

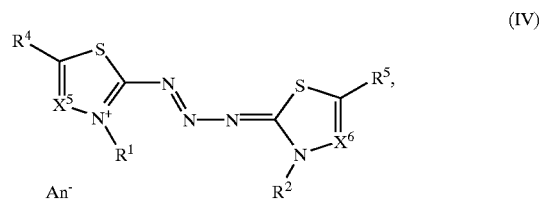

(IV)

wherein $R^1$ and $R^2$ independently of one another represent $C_1$- to $C_{16}$-alkyl, $C_3$- to $C_6$-alkenyl, $C_5$- to $C_7$-cycloalkyl or $C_7$- to $C_{16}$-aralkyl, $X^5$ represents N or C—$R^6$, $X^6$ represents N or C—$R^7$, $R^4$ to $R^7$ independently of one another represent hydrogen, $C_1$- to $C_4$-alkyl, $C_1$- to $C_4$-alkoxy, cyano, $C_1$- to $C_4$-alkoxycarbonyl, nitro, mono- or bis-$C_1$- to $C_4$-alkylamino, N—$C_1$- to $C_4$-alkyl-N—$C_7$- to $C_{15}$-aralkylamino, N—$C_1$- to $C_4$-alkyl-N—$C_5$- to $C_{17}$-cyclo-alkylamino, N—$C_1$- to $C_4$-Alkyl-N—$C_6$- to $_{10}$-arylamino, $C_6$- to $C_{10}$-arylamino, pyrrolidino, piperidino or morpholino or $R^4$; $R^6$ and $R^5$; $R^7$ independently of one another form a —CH=CH—CH=CH— bridge, which can be substituted by methyl, chlorine, methoxy or cyano, and $An^-$ represents an anion.

5. The use of triazacyanines in the information layer of recordable optical data storage media, wherein the triazacyanines have an absorption maximum $\lambda_{max2}$ in the range from 420 to 650 nm.

6. The use of triazacyanines in the information layer of recordable optical data storage media, wherein the data storage media are recorded on and read using a blue laser light.

7. A process for producing the optical data storage media according to claim 1, which is characterized in that a preferably transparent substrate, which has optionally already been coated with a reflecting layer, is coated with the triazacyanines, optionally in combination with suitable binders and additives and optionally suitable solvents, and is optionally provided with a reflecting layer, additional intermediate layers and optionally a protective layer or an additional substrate or a top layer.

8. Optical data storage media according to claim 1 which have been recorded on using blue or red, in particular blue light, and especially laser light.

* * * * *